(12) United States Patent
Fujioka et al.

(10) Patent No.: US 11,964,939 B2
(45) Date of Patent: Apr. 23, 2024

(54) AROMATIC TETRACARBOXYLIC ACID COMPOUND

(71) Applicant: HONSHU CHEMICAL INDUSTRY CO., LTD., Tokyo (JP)

(72) Inventors: Rie Fujioka, Wakayama (JP); Masahiko Saibara, Wakayama (JP)

(73) Assignee: HONSHU CHEMICAL INDUSTRY CO., LTD., Tokyo (JP)

(*) Notice: Subject to any disclaimer, the term of this patent is extended or adjusted under 35 U.S.C. 154(b) by 510 days.

(21) Appl. No.: 17/282,328

(22) PCT Filed: Oct. 7, 2019

(86) PCT No.: PCT/JP2019/039431
§ 371 (c)(1),
(2) Date: Apr. 1, 2021

(87) PCT Pub. No.: WO2020/080157
PCT Pub. Date: Apr. 23, 2020

(65) Prior Publication Data
US 2021/0347723 A1    Nov. 11, 2021

(30) Foreign Application Priority Data
Oct. 19, 2018   (JP) ................................. 2018-197426

(51) Int. Cl.
*C07C 69/80* (2006.01)

(52) U.S. Cl.
CPC .................................. *C07C 69/80* (2013.01)

(58) Field of Classification Search
CPC ..................................................... C07C 69/80
See application file for complete search history.

(56) References Cited

U.S. PATENT DOCUMENTS

2013/0345352 A1   12/2013   Ward et al.

FOREIGN PATENT DOCUMENTS

| JP | H04-29986 | * | 1/1992 | .......... C07D 307/89 |
| JP | H0429986 A | | 1/1992 | |
| JP | H06322254 A | | 11/1994 | |
| JP | 2004352670 A | | 12/2004 | |
| JP | 2006-206486 | * | 8/2006 | .......... C07D 307/89 |
| JP | 2006206486 A | | 8/2006 | |
| JP | 2011111415 A | | 6/2011 | |
| JP | 2014503669 A | | 2/2014 | |

OTHER PUBLICATIONS

Hernandez et al., SIDS initial assessment report for 15th SIAM, Trimellitic Anhhydride and Trimellitic Acid, OECD SIDS, 151 pages (Year: 2002).*
Notification Concerning Transmittal of International Preliminary Report on Patentability (PCT/IB/326) and Notification of Transmittal of Translation of the International Preliminary Report on Patentability (PCT/IB/338) dated Apr. 29, 2021, with International Preliminary Report on Patentability (PCT/IB/373) and Written Opinion of the International Searching Authority (PCT/ISA/237), for corresponding international application PCT/JP2019/039431 (11 pages).
International Search Report (ISR) dated Nov. 26, 2019, issued for International application No. PCT/JP2019/039431. (1 page).

* cited by examiner

*Primary Examiner* — Yate' K Cutliff
(74) *Attorney, Agent, or Firm* — Law Office of Katsuhiro Arai

(57) ABSTRACT

An object of the present invention is to provide a novel compound that provides a curing agent that is less likely to volatilize during curing reaction and is excellent in various properties such as heat resistance. As a solution, an aromatic tetracarboxylic acid compound represented by formula (I) below is provided.

[Chem. 1]

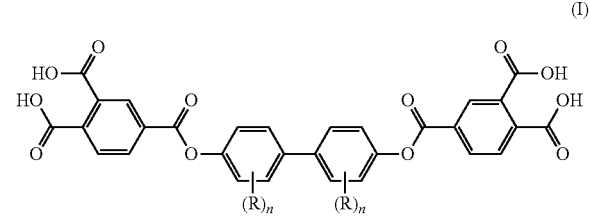

(In the formula, each R independently represents an alkyl group having 1 to 4 carbon atoms or an alkoxy group having 1 to 4 carbon atoms, and each n independently represents 0 or an integer of 1 to 4.)

2 Claims, No Drawings

AROMATIC TETRACARBOXYLIC ACID COMPOUND

CROSS-REFERENCE TO RELATED APPLICATIONS

This application is the U.S. National Phase under 35 U.S.C. § 371 of International Application PCT/JP2019/039431, filed Oct. 7, 2019, which claims priority to Japanese Patent Application No. JP2018-197426, filed Oct. 19, 2018. The International Application was published under PCT Article 21(2) in a language other than English.

TECHNICAL FIELD

The present invention relates to a novel aromatic tetracarboxylic acid compound.

BACKGROUND ART

Carboxylic acid compounds, which are widely used in the fields of organic chemistry and polymer chemistry, are compounds useful in various fields of industrial applications, such as fine chemicals, raw materials for pharmaceuticals and agrochemicals, raw materials for resins and plastics, electronic information materials, and optical materials. In particular, polycarboxylic acids and anhydrides thereof are compounds useful as monomers for polymeric materials, such as raw materials, for example, for polyimides, or as polyester resin modifiers and epoxy resin curing agents because they are excellent in various properties such as heat resistance, good mechanical and electrical properties, or chemical resistance, readily form condensates, and have high reactivity.

Many saturated hydrocarbon acid anhydrides, such as methylhexahydrophthalic anhydride and methyltetrahydrophthalic anhydride, are being used as curing agents for epoxy resins because cured products having high light resistance are provided. However, these curing agents have high vapor pressures and thus partially volatilize during curing reaction, and when thermally cured in an open system, the curing agents volatilize into the atmosphere to cause problems such as pollution of a production line as well as adverse effects on operators.

CITATION LIST

Patent Literature

PTL 1: Japanese Unexamined Patent Application Publication No. 2004-352670
PTL 2: Japanese Unexamined Patent Application Publication No. 2011-111415
PTL 3: Japanese Unexamined Patent Application Publication (Translation of PCT Application) No. 2014-503669

SUMMARY OF INVENTION

Technical Problem

An object of the present invention is to provide a novel compound that provides a curing agent that, when used as a curing agent for an epoxy resin, is less likely to volatilize during curing reaction and is excellent in various properties such as heat resistance.

Solution to Problem

To solve the above problems, the present inventors have conducted intensive studies and found that an aromatic tetracarboxylic acid compound having a biphenyl skeleton, when used as an epoxy resin curing agent, suppresses volatilization during curing reaction and provides a cured product having high heat resistance, thereby completing the present invention.

The present invention is as follows.
1. An aromatic tetracarboxylic acid compound represented by formula (I) below.

[Chem. 1]

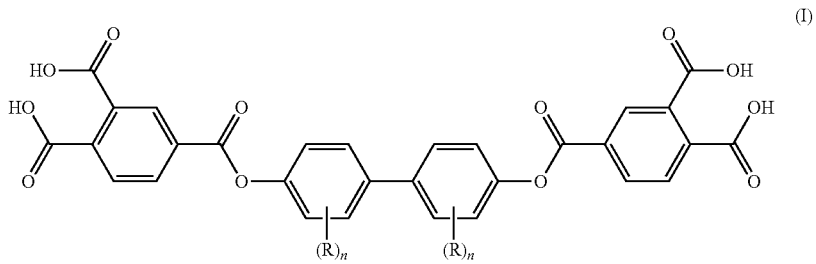

(In the formula, each R independently represents an alkyl group having 1 to 4 carbon atoms or an alkoxy group having 1 to 4 carbon atoms, and each n independently represents 0 or an integer of 1 to 4.)

Advantageous Effects of Invention

According to the present invention, a novel aromatic tetracarboxylic acid compound having a biphenyl skeleton is provided. The novel aromatic tetracarboxylic acid compound, when used as an epoxy resin curing agent, can reduce volatilization during curing reaction, and thus can suppress, for example, pollution of a production line and deterioration of a work environment. A resin obtained using the novel aromatic tetracarboxylic acid compound of the present invention as an epoxy resin curing agent is excellent, for example, in heat resistance and flame resistance, and thus is suitable for use in resin manufacturing of molded electrical and electronic components, automotive components, laminated materials, paints, resist inks, etc.

DESCRIPTION OF EMBODIMENTS

An aromatic tetracarboxylic acid compound of the present invention is represented by formula (I) below.

[Chem. 2]

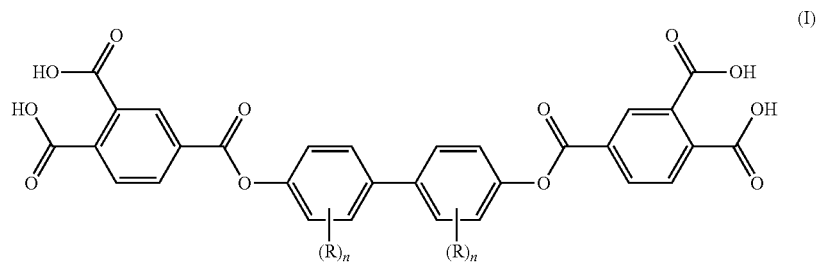

(In the formula, each R independently represents an alkyl group having 1 to 4 carbon atoms or an alkoxy group having 1 to 4 carbon atoms, and each n independently represents 0 or an integer of 1 to 4.)

The chemical structure of "4-({4-[4-(3,4-dicarboxyphenylcarbonyloxy)-2,3,5-trimethylphenyl]-2,3,6-trimethylphenyl]oxycarbonyl}benzene-1,2-dicarboxylic acid" (hereinafter referred to as "Compound A"), which is a preferred compound of the above formula (I), is shown below.

[Chem. 3]

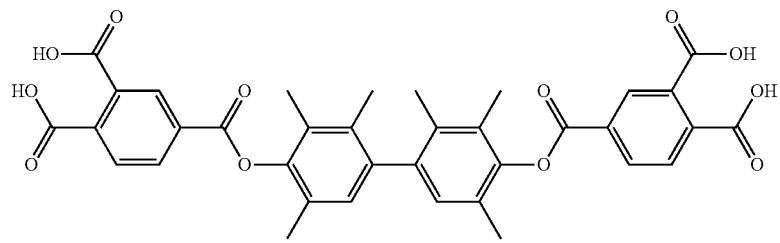

Regarding how to produce the aromatic tetracarboxylic acid compound of the present invention represented by the above formula (I), there is no particular limitation on starting materials, reaction conditions, etc., and, for example, the aromatic tetracarboxylic acid compound can be readily obtained by hydrolyzing an aromatic tetracarboxylic dianhydride, as shown by the following reaction formula.

[Chem. 4]

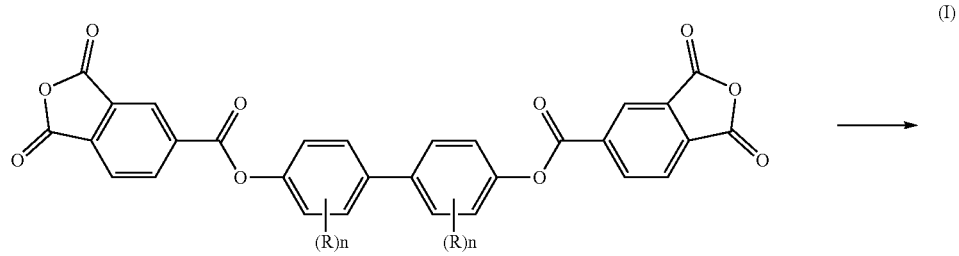

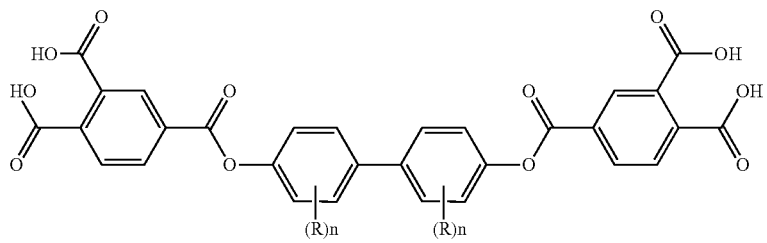

(In the formula, R and n are as defined in formula (I).)

For the reaction conditions under which the aromatic tetracarboxylic dianhydride is hydrolyzed, a standard method of hydrolyzing an alkyl ester to form a carboxylic acid can be used. Examples of acids used include inorganic acids such as phosphoric acid, hydrochloric acid, and sulfuric acid and sulfonic acids such as methanesulfonic acid and p-toluenesulfonic acid. Of these, a method using phosphoric acid is convenient. The amount of phosphoric acid used is preferably about 0.1 to 5 wt %, more preferably 1 to 3 wt %, based on the amount of the aromatic tetracarboxylic dianhydride.

Any reaction solvent may be used as long as it is a water-miscible solvent such as methanol, ethanol, 1-propanol, 2-propanol, tetrahydrofuran, or N-methylpyrrolidone. Of these, tetrahydrofuran, particularly, tetrahydrofuran containing 2,6-di-t-butyl-4-methylphenol (BHT) as a stabilizer is most suitable. The amounts of tetrahydrofuran and water used are both preferably three to five times the weight of the aromatic tetracarboxylic dianhydride.

The hydrolysis reaction is performed by adding water and a catalytic amount of phosphoric acid to a solution of the aromatic tetracarboxylic dianhydride in tetrahydrofuran and stirring the resultant with heating at a reaction temperature in the range of 30° C. to 65° C., preferably in the range of 40° C. to 60° C., whereby the object can be obtained.

The reaction time correlates with the reaction temperature and is practically 1 to 40 hours, more preferably 2 to 30 hours.

For the thus-obtained final reaction mixture containing the aromatic tetracarboxylic acid compound of the present invention, when a crystal or solid of the object is precipitated or deposited after completion of the reaction, the object can be obtained in such a manner that the reaction solution is filtered as it is or after being cooled, and the resulting crystal is dried. When a crystal or solid of the object is not precipitated or deposited at the completion of the reaction, the object can be collected from the final reaction mixture according to a known method. For example, the object can be precipitated or deposited by adding the final reaction mixture dropwise into a large amount of poor solvent or adding a poor solvent to the final reaction mixture. The object obtained can optionally be recrystallized or washed with water according to a known method to produce a high-purity product.

EXAMPLES

The present invention will now be described more specifically with reference to an example.

The yield in the following example was measured by gel permeation chromatography (GPC).

<Method of Analysis>
1. Gel Permeation Chromatography Measurement
   Apparatus: HLC-8320GPC manufactured by Tosoh Corporation
   Flow rate: 1.0 ml/min, mobile phase: tetrahydrofuran, injection volume: 100 μl
   Column: one TSKgel HXL-L guardcolumn, two TSKgel G2000HXL columns, one TSKgel G3000HXL column, one TSKgel G4000HXL column
   Detector: RI
   Column temperature: 40° C.
   Moving bed solvent: BHT-containing tetrahydrofuran <Example 1> (Synthesis of Aromatic Tetracarboxylic Acid Compound "Compound A")

In a 500 mL four-necked flask equipped with a stirrer, a thermometer, and a condenser, 50.7 g of 4,4'-bis(1,3-dioxo-1,3-dihydroisobenzofuran-5-ylcarbonyloxy)-2,2',3,3',5,5'-hexamethylbiphenyl, 152.1 g of BHT-containing tetrahydrofuran, 152.1 g of water, and 0.507 g of 85% phosphoric acid were placed and heated to 40° C. with stirring in a nitrogen gas atmosphere, after which a reaction was run for 25 hours while maintaining the temperature at 40° C. Furthermore, the temperature was raised to 50° C., and the reaction was run for 4 hours. Thereafter, 85 g of water was added dropwise. During the dropwise addition, a solid precipitated at room temperature. The precipitated solid was separated by filtration and dried to obtain 48.9 g (yield: 91.4 mol %) of a white to beige solid with a purity of 96.8% (GPC measurement data analysis).

From the results of $^1$H-NMR and $^{13}$C-NMR analyses, the solid obtained was identified to be "Compound A" having the above chemical structure.

$^1$H-NMR (300 MHz) measured ppm (solvent: deuterated DMSO): 1.97 (s, 6H: a), 2.11 (s, 6H: b), 2.14 (s, 6H: c), 6.97 (s, 2H, d), 7.89-7.91 (d, 2H, e), 8.40-8.43 (dd, 2H, f), 8.48 (s, 2H: g), 13.60 (s, 4H: h).

[Chem. 5]

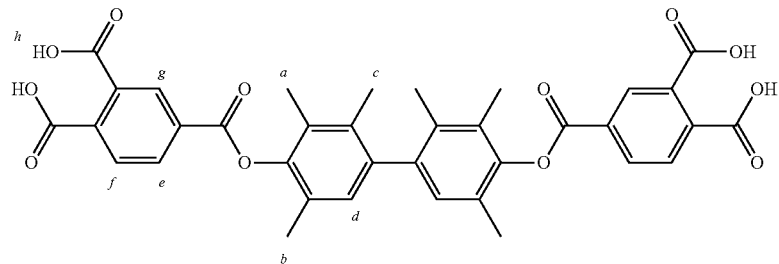

$^{13}$C-NMR (300 MHz) measured ppm (solvent: deuterated methanol): 11.96 (a), 14.99 (b), 15.59 (c), 126.80-139.79, 147.10 (p), 163.28 (q), 168.10 (r), 169.26 (z).

[Chem. 6]

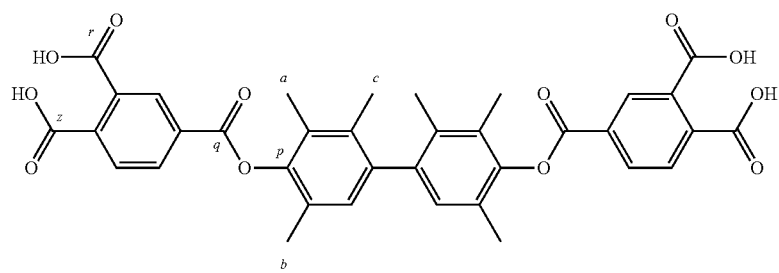

The invention claimed is:

1. An aromatic tetracarboxylic acid compound represented by formula (I) below:

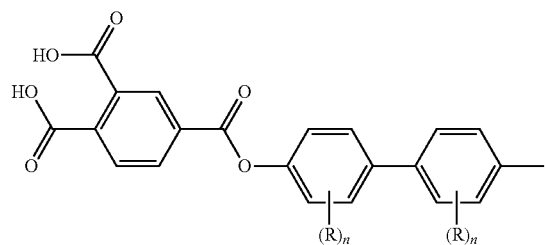

(I)

-continued

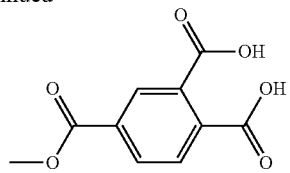

wherein each R independently represents an alkyl group having 1 to 4 carbon atoms or an alkoxy group having 1 to 4 carbon atoms, and each n represents 3.

2. The aromatic tetracarboxylic acid compound according to claim 1, wherein each R represents a methyl group.

* * * * *